United States Patent [19]

Niebur

[11] 4,257,134
[45] Mar. 24, 1981

[54] BEEHIVE

[76] Inventor: Mark J. Niebur, P.O. Box 753, Malta, Mont. 59538

[21] Appl. No.: 104,002

[22] Filed: Dec. 17, 1979

[51] Int. Cl.³ ............................................. A01K 47/00
[52] U.S. Cl. ................................................. 6/1; 6/11
[58] Field of Search .......................... 6/1, 2 R, 10, 11; 229/DIG. 2; 119/1, 15; 210/494 R, 150

[56] References Cited

U.S. PATENT DOCUMENTS

| | | | |
|---|---|---|---|
| 1,020,567 | 3/1912 | Moeller | 229/DIG. 2 |
| 3,486,485 | 12/1969 | Kahanick | 119/1 |
| 3,936,894 | 2/1976 | Barber | 6/11 |
| 4,172,336 | 10/1979 | Aylor | 119/1 X |
| 4,207,637 | 6/1980 | Niebur | 6/1 |

Primary Examiner—Gene Mancene
Assistant Examiner—Robert P. Swiatek
Attorney, Agent, or Firm—Arthur L. Urban

[57] ABSTRACT

A beehive including a housing comprising a bottom portion, longitudinal sidewall portions extending upwardly from the bottom portion, retainers associated with the upper free edges of the sidewall portions, removable end sections extending between the sidewall portions, the bottom portion including a plurality of spaced openings and a plurality of rib members located between the openings, a plurality of cellular strips disposed within the housing and extending between the sidewall portions, a plurality of plastic strips disposed within the housing and extending between the sidewall portions, the plastic strips being corrugated transversely of their length, the plastic strips being disposed between the cellular strips in an alternating relationship, the cellular and plastic strips not being bonded to each other but being separable and independent of one another, the strips being disposed closely adjacent to each other, the strips substantially completely filling the housing between the end sections, and a common backing member disposed between the bottom portion and the adjacent edges of the strips.

12 Claims, 3 Drawing Figures

BEEHIVE

This invention relates to a novel beehive and more particularly relates to a novel hive which is especially useful for leaf cutter bees.

The use of bees to pollinate various crops is well known. To ensure that a high degree of cross pollination is achieved, it is common to place hives for bees in the fields with the growing crops. Cross-pollination with bees which are placed in the fields can produce a major increase in crop yield.

Alfalfa seed growers rely heavily on induced bee pollination to increase the yield of their crop. However, common honey bees cannot be used in the pollination of growing alfalfa. Leaf cutter bees are the only reliable means of cross-pollination growing alfalfa. Since approximately 20,000 leaf cutter bees must be placed in each acre of growing alfalfa to achieve optimum pollination, the harvesting and care of the bees is a very important part of the growing of alfalfa seed.

A number of different hives have been proposed for use by alfalfa growers with leaf cutter bees. For example, U.S. Pat. No. 3,191,199 describes a hive formed from grooved wooden boards. When the boards are assembled with the grooves in a matching relationship, a large number of holes or nests are formed. The bees lay their eggs in the passages, seal each passage over and continue in this manner until each passage is filled with eggs and the individual eggs sealed from each other. Generally, the eggs are hatched into larvae by the time the pollination period is completed and the hives are removed from the fields. The hives then are opened and the larvae removed and stored until the next season.

While the grooved board hives were designed to facilitate removal of the larvae, even this construction leaves much to be desired. The hives must be taken apart and the larvae removed from the individual grooves of each board. Then, the boards must be inspected for parasite infestation and if such is found, the boards treated with a parasite killer before reassembling the boards to form the hive again. The boards forming the hive must be reassembled very carefully to avoid unevenness or gaps which may increase the severity of reinfestation by the parasites.

It has been proposed to make disposable hives which can be discarded each season after the larvae have been removed therefrom. This has the advantage that the hives can be torn apart to remove the larvae rather than using care in their removal so the hives can be reused. Unfortunately, this is not a desirable solution since bees prefer to lay their eggs in hives which have been used by them in previous seasons. If new hives are used each year, there will be a lower yield of bee larvae per acre than can be achieved with used hives.

Since bees are in short supply and are not readily available on the open market, alfalfa seed growers go to great efforts to be sure that they obtain maximum yields of bees from their fields. These efforts even include the extra work on their part in the cleaning and assembly of hives by hand. In view of the problems associated with present beehives, however, alfalfa seed growers are very desirous of finding a new type of hive which will reduce the time and labor required for taking apart, cleaning and reassembly of present hives.

The present invention provides a novel beehive which simplifies the cleaning and assembly of the hive components. The beehive of the invention enables the hive to be cleaned and reassembled mechanically with a minimum of hand labor. Also, the hive design facilitates removal of the larvae with a minimum of damage to the larvae and to the hive components. Thus, the beehive of the invention provides high yields of bees in reuseable hives while significantly reducing the work connected with the cleaning of the hives. Further, the design of the beehive reduces parasite infestation. In addition, the design of the hive allows the hive components to be treated conveniently during larvae removal to further reduce further parasite infestation. Moreover, the beehive design of the invention permits easy replacement of components during larvae removal. Also, the beehive is simple in design and can be fabricated from commercially available materials relatively inexpensively.

Other benefits and advantages of the novel beehive of the present invention will be apparent from the following description and the accompanying drawings in which.

Figure 1:
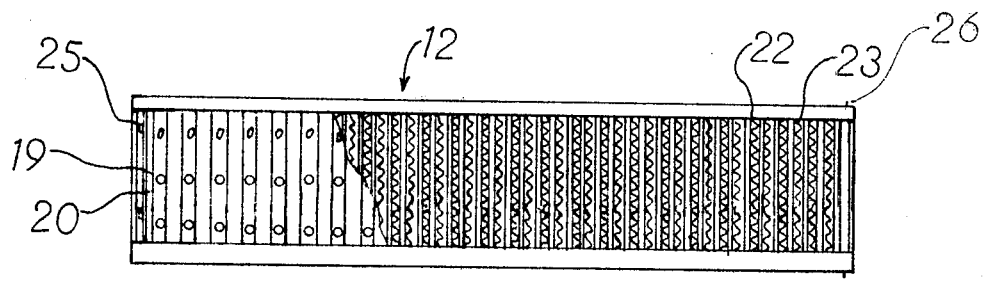
FIG. 1 is a front view partially in section of one form of the beehive of the invention.
Figure 2:
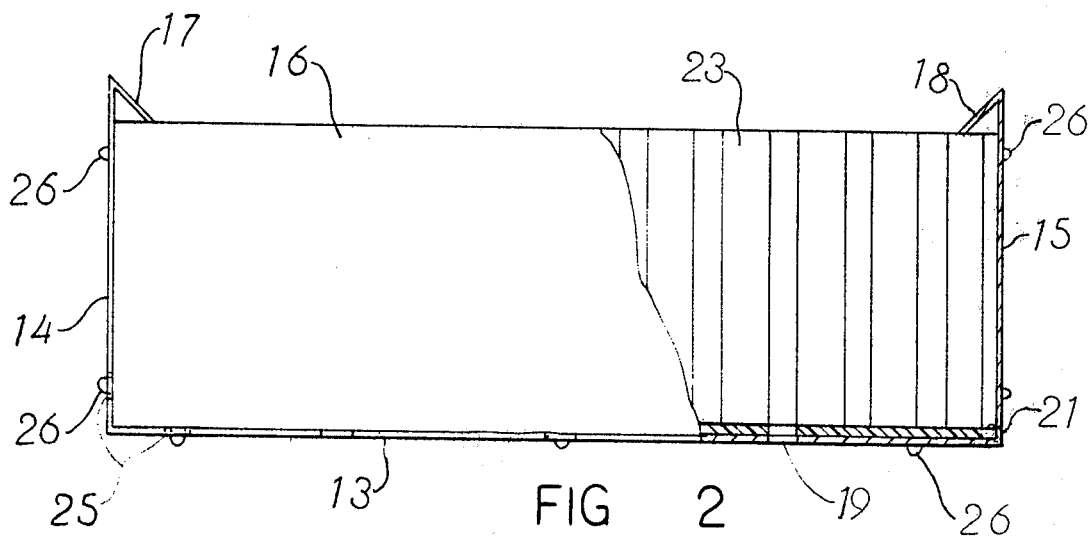
FIG. 2 is an end view partially in section of the beehive shown in FIG. 1.

As shown in the drawings, one form of the novel beehive of the present invention includes a housing member 12. Housing 12 includes a bottom portion 13 and longitudinal sidewall portions 14 and 15 and removable end sections 16. Sidewall portions 14 and 15 extend from the bottom portion 13 with the free edges of the sidewall portions having retainer means associated therewith. The retainer means as shown in the drawings advantageously includes inwardly extending flange sections 17 and 18 that preferably extend inwardly and downwardly from the sidewall portions 14 and 15 toward the bottom portion 13. Preferably, the distance between the sidewall portions 14 and 15 is greater than the distance between the bottom portion 13 and the retainer means.

The bottom portion 13, sidewall portions 14 and 15 and the retainer means of housing 12 advantageously are a unitary structure preferably formed by molding. The housing 12 may be molded continuously such as by extrusion molding a plastic material and cutting the continuous extruded form into desired lengths.

The bottom portion 13 of the housing 12 includes a plurality of spaced openings 19 and a plurality of rib members 20 located between the openings. The openings 19 in the bottom portion 13 advantageously are arranged in rows as shown. Preferably, the rib members 20 are disposed transversely of the sidewall portions 14 and 15 between the rows. A common backing member 21 is disposed over the inside surface of bottom portion 13. Backing member 21 preferably is a cellular structure.

A plurality of cellular spacer strips 22 are disposed within the housing 12. The cellular strips 22 extend between the sidewall portions 14 and 15 of the housing 12. Also, a plurality of corrugated plastic strips 23 are disposed within housing 12 and extend between the sidewall portions 14 and 15.

The cellular strips 22 and the corrugated plastic strips 23 are disposed in an alternating interleaved relationship. The cellular strips 22 and the corrugated plastic strips 23 are not bonded to each other but are individually separable and independent of one another. The cellular strips 22 advantageously are rigid strips although flexible strips may be employed. The cellular strips 22 preferably are between about one-eighth and one-half inch in thickness. The cellular strips may be formed of a natural or synthetic foam material as desired with polymeric foams such polyurethanes being preferred because of their greater durability and their resistance to parasite infestation.

The plastic strips 23 are corrugated transversely of their length so that the corrugations provide open passages extending from the free surface of the hive. The corrugations of the plastic strips 23 advantageously are spaced less than about one-half inch apart, that is, as measured along a perpendicular straight line between the centers of adjacent up and down corrugations. Thus, the distance between the centers of two up corrugations would be twice the distance between adjacent up and down corrugations. The depth of each corrugation advantageously also is less than about one-half inch. Preferably, the spacing between the corrugations and also the depth thereof each are between about three-sixteenths and three-eighths inch.

The plastic strips 23 may be formed of a suitable polymeric material such as polystyrene, polyolefins, polyamides, polyesters, polyacrylics and the like. Advantageously, the housing 12 also is molded from one of the above materials. Polystyrene is particularly suitable for the fabrication of the plastic strips 23 and the housing 12 because of its low cost, durability, light weight and ease of cleaning.

The beehive of the invention as shown in the drawings is assembled by inserting cellular strips 22 and corrugated plastic strips 23 into an open end of housing 12 after backing member 21 has been placed over bottom portion 13. The strips 22 and 23 are inserted alternately with the side edges of each strip in contact with the sidewall portions 14 and 15, the bottom edge against backing member 21 and the upper corner of the strips under flange sections 17 and 18. When the housing 12 is filled with the strips, the housing is closed with an end section 16. End sections 16 may be secured to housing 12 with suitable fastening means shown as protuberances 20 that engage openings 25 located adjacent the ends of bottom 13 and sidewalls 14 and 15.

The assembled hive is placed in a field in which bees have been released for pollination of a crop such as alfalfa. The bees deposit eggs in the passages created by the corrugations in the assembled cellular strip 22 and the adjoining corrugated plastic strips 23 of the hive. When pollination of the crop is completed, the hive is removed from the field for cleaning and storage until the next growing season.

Figure 3:
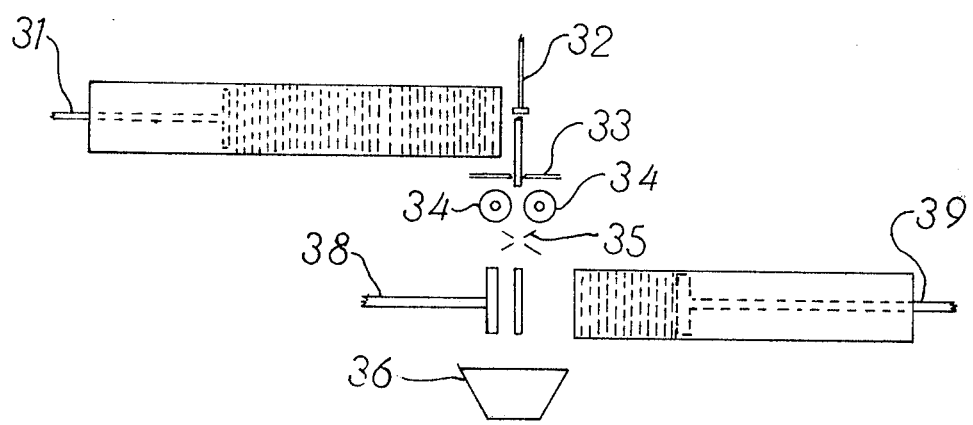
FIG. 3 is a schematic illustration of apparatus for cleaning the beehive shown in FIG. 1.

The beehive of the present invention may be cleaned to remove the eggs and larvae simply and conveniently. While the cleaning may be accomplished with hand labor, it can be performed more advantageously mechanically such as with apparatus shown in FIG. 3. A beehive is positioned with the bottom portion 13 of the housing 12 in an up orientation. An indexing means 31 located at one end of housing 12 advances the strips 22 and 23 from the opposite end of the housing 12 at a rate such that one strip is released from the housing at a time.

The freed strip then is pushed by advancing mechanism 32 between blades 33 disposed and between rotating brushes 34 disposed on either side of the path of the strip. The blades 33 are spaced to scrape eggs and larvae from the cellular strips 22 while allowing the corrugated strips 23 to pass therebetween. The brushes 34 are more closely spaced to enter the corrugations of the strips 23 and remove the eggs and larvae therefrom. The eggs and larvae fall into a suitable collector 36.

The cleaned strips 22 and 23 may be treated to kill any parasites present and to inhibit future infestation. Suitable chemicals may be applied to the strips through nozzles 35. If any strips are found to be damaged, they may be discarded during the cleaning operation, with replacements being added as the hive is being reassembled.

After being cleaned, the strips are transferred to a second housing positioned adjacent the first housing and the cleaning apparatus. The cleaned strips may be inserted into an open end of the second housing with a guiding mechanism 38. A support member 39 may be disposed in the opposite end of the second housing to hold the strips in proper position as they are reassembled. When all of the strips have been cleaned and transferred to the second housing, any replacements required may be added and end sections 16 secured in place. The cleaned hive then is stored until needed and again placed in a field for use by the bees.

The above description and the accompanying drawings show that the present invention provides a novel beehive which can be cleaned and reused simply and conveniently. The design of the beehive of the invention enables the hive to be cleaned and reassembled mechanically with a minimum of hand labor. In addition, the hive design facilitates removal of the larvae with a minimum of damage to the larvae and to the hive components. As a result, the beehive of the invention provides high yields of bees. Since the bee larvae can be removed from the hive easily, the hives can be reused repeatedly.

Another advantage of the novel beehive of the invention is the significant reduction in parasite infestation. Further, the design of the hive permits the hive components to be treated conveniently after larvae removal to further reduce future parasite infestation.

The beehive of the present invention also is simple in design and can be fabricated from commercially available materials relatively inexpensively. Moreover, the beehive design allows convenient replacement of components during cleaning.

It will be apparent that various modifications may be made in the particular beehive and cleaning apparatus described in detail above and shown in the drawings within the scope of the invention. For example, the size and configuration of the hive may be changed to meet specific requirements. Also, the dimensions of the cellular strip and the corrugated plastic strip may be different if desired. Further, the cleaning method and apparatus may be modified to accomodate changes in the hive structure. Therefore, the scope of the invention is to be limited only by the following claims.

What is claimed is:

1. A beehive including a housing comprising a bottom portion, longitudinal sidewall portions extending upwardly from said bottom portion, retainer means associated with the upper free edges of said sidewall portions, removable end sections extending between said sidewall portions, said bottom portion including a plurality of spaced openings and a plurality of rib members located between said openings, a plurality of spacer strips disposed within said housing and extending between said sidewall portions, a plurality of plastic strips disposed with said housing and extending between said sidewall portions, said plastic strips being corrugated transversely of their length, said plastic strips being disposed between said spacer strips in an alternating relationship, said spacer and plastic strips not being bonded to each other but being separable and independent of one another, said strips being disposed closely adjacent to each other, said strips substantially completely filling said housing between said end sections, and a common backing member disposed between said bottom portion and the adjacent edges of said strips.

2. A beehive according to claim 1 wherein said bottom portion, said sidewall portions and said retainer means are a unitary structure.

3. A beehive according to claim 1 wherein said retainer means includes inwardly extending flange sections.

4. A beehive according to claim 3 wherein said flange sections extend inwardly and downwardly toward said bottom portion.

5. A beehive according to claim 1 wherein said common backing member is a cellular structure.

6. A beehive according to claim 1 wherein said openings in said bottom portion are arranged in rows.

7. A beehive according to claim 6 wherein said rib members are disposed transversely of said sidewall portions.

8. A beehive according to claim 1 wherein the distance between said sidewall portions is greater than the distance between said bottom portion and said retainer means.

9. A beehive according to claim 1 wherein said spacer strips are foam strips between about one-eighth and one-half inch in thickness.

10. A beehive according to claim 1 wherein said corrugations of said plastic strips are spaced apart less than about one-half inch and have a depth less than about one-half inch.

11. A beehive according to claim 10 wherein said corrugations are spaced apart between about three-sixteenths and three-eighths inch and have a depth between about three-sixteenths and three-eighths inch.

12. A method of cleaning a beehive including a housing with a plurality of spacer strips and a plurality of corrugated plastic strips disposed in an alternating separable relationship, the steps comprising: indexing said strips individually from said housing, simultaneously scraping both sides of said individual strips to remove larvae therefrom while transferring them to a second housing, reinserting said cleaned strips individually into an open end of said second housing in an alternating relationship, and closing said open end of said housing with an end section.

* * * * *